(12) United States Patent
Cheng et al.

(10) Patent No.: US 11,278,429 B2
(45) Date of Patent: Mar. 22, 2022

(54) APPARATUS FOR INVITRO CONTROL OF DEGRADATION RATE OF ARTIFICIAL BONE, DEGRADATION METHOD, AND ARTIFICIAL BONE

(71) Applicants: FUZHOU BOE OPTOELECTRONICS TECHNOLOGY CO., LTD., Fuzhou (CN); BOE TECHNOLOGY GROUP CO., LTD., Beijing (CN)

(72) Inventors: Li Cheng, Beijing (CN); Jianming Huang, Beijing (CN); Xiaobo Jia, Beijing (CN); Wanping Pan, Beijing (CN); Qiusheng Lin, Beijing (CN); Ying Wang, Beijing (CN); Yabin Lin, Beijing (CN); Weiqiang Li, Beijing (CN); Aihua Zhu, Beijing (CN); Xuezhen Su, Beijing (CN); Hailong Yu, Beijing (CN); Yifeng Su, Beijing (CN); Xiaoying Lu, Beijing (CN)

(73) Assignees: FUZHOU BOE OPTOELECTRONICS TECHNOLOGY CO., LTD., Fujian (CN); BOE TECHNOLOGY GROUP CO., LTD., Beijing (CN)

( * ) Notice: Subject to any disclaimer, the term of this patent is extended or adjusted under 35 U.S.C. 154(b) by 315 days.

(21) Appl. No.: 16/518,734

(22) Filed: Jul. 22, 2019

(65) Prior Publication Data
US 2020/0129310 A1    Apr. 30, 2020

(30) Foreign Application Priority Data

Oct. 25, 2018  (CN) .......................... 201811250177.1

(51) Int. Cl.
*A61F 2/46* (2006.01)
*A61F 2/28* (2006.01)
(Continued)

(52) U.S. Cl.
CPC .............. *A61F 2/4603* (2013.01); *A61F 2/28* (2013.01); *A61F 2/3094* (2013.01); *C23C 8/02* (2013.01);
(Continued)

(58) Field of Classification Search
CPC .... A61F 2/28; A61F 2/4603; A61F 2002/469; A61F 2002/4698; A61N 2/02; A61N 2/006; A61N 1/32
See application file for complete search history.

(56) References Cited

U.S. PATENT DOCUMENTS 3,890,953 A * 6/1975 Kraus ........................ A61F 2/30
600/14
4,266,533 A * 5/1981 Ryaby ...................... A61N 2/02
600/14
(Continued)

FOREIGN PATENT DOCUMENTS

CN         1255387 A      6/2000
CN         1857744 A     11/2006
(Continued)

OTHER PUBLICATIONS

First Chinese Office Action dated Mar. 5, 2020, received for corresponding Chinese Application No. 201811250177.1, 20 pages.
(Continued)

*Primary Examiner* — Brian A Dukert
(74) *Attorney, Agent, or Firm* — Kinney & Lange, P.A.

(57) ABSTRACT

An apparatus for controlling a degradation rate of an artificial bone in vitro, a degradation method, and an artificial bone are disclosed. The apparatus includes: a variable resis-
(Continued)

tor; and a wearable component, comprising: a metal wire electrically connected in series with the variable resistor and configured to generate an alternating magnetic field; and an insulating textile layer by which the outside of the metal wire is covered.

18 Claims, 2 Drawing Sheets

(51) Int. Cl.
  *A61F 2/30* (2006.01)
  *C23C 8/02* (2006.01)
  *C23C 8/12* (2006.01)
  *H01C 10/00* (2006.01)

(52) U.S. Cl.
  CPC .......... *C23C 8/12* (2013.01); *A61F 2002/469* (2013.01); *A61F 2310/00023* (2013.01); *A61F 2310/00041* (2013.01); *H01C 10/00* (2013.01)

(56) References Cited

U.S. PATENT DOCUMENTS

| | | | | |
|---|---|---|---|---|
| 4,993,413 | A * | 2/1991 | McLeod | A61N 1/321 600/13 |
| 5,951,459 | A * | 9/1999 | Blackwell | A61N 2/02 600/13 |
| 7,297,100 | B2 * | 11/2007 | Thomas | A61N 1/16 600/14 |
| 7,963,904 | B2 * | 6/2011 | Delisle | A61N 2/02 600/14 |
| 8,372,144 | B2 | 2/2013 | Mueller et al. | |
| 8,623,097 | B2 * | 1/2014 | Gerold | A61B 5/4839 623/24 |

FOREIGN PATENT DOCUMENTS

| | | |
|---|---|---|
| CN | 101219068 A | 7/2008 |
| CN | 101249286 A | 8/2008 |
| CN | 101264339 A | 9/2008 |
| CN | 201189358 Y | 2/2009 |
| CN | 102784415 A | 11/2012 |
| CN | 104208753 A | 12/2014 |
| CN | 106966702 A | 7/2017 |
| CN | 108310657 A | 7/2018 |

OTHER PUBLICATIONS

First Chinese Office Action dated Oct. 22, 2020, received for corresponding Chinese Application No. 201811250177.1.

* cited by examiner

APPARATUS FOR INVITRO CONTROL OF DEGRADATION RATE OF ARTIFICIAL BONE, DEGRADATION METHOD, AND ARTIFICIAL BONE

CROSS-REFERENCE TO RELATED APPLICATION(S)

This application claims priority to the Chinese Patent Application No. CN 201811250177.1, filed on Oct. 25, 2018, entitled "APPARATUS FOR INVITRO CONTROL OF DEGRADATION RATE OF ARTIFICIAL BONE, DEGRADATION METHOD, AND ARTIFICIAL BONE", which is incorporated herein by reference in its entirety.

TECHNICAL FIELD

The present disclosure relates to the field of biomedical technology, and more particularly, to an apparatus for invitro control of a degradation rate of an artificial bone, a degradation method, and an artificial bone.

BACKGROUND

In the field of orthopedics, bone defects for various reasons such as severe trauma, bone tumors, osteomyelitis etc. are very common. Bone repair materials which are commonly used currently comprise autologous bones and metal prostheses. The autologous bones increase trauma and pain of patients, and the metal prostheses have problems such as looseness, breakage etc. Therefore, repair of the bone defects through transplantation of an artificial bone has become a medical focus. The artificial bone refers to an artificial biological material which may replace a human bone or repair bone tissue defects. Since the human bone has a tissue regeneration function, in some cases, the bone may be repaired by itself through the tissue regeneration function. However, in many cases, the human bone may not be repaired by itself. In these cases, the human bone needs to be healed with the aid of an artificial bone, and the artificial bone implanted in a human body may be eliminated from the human body through self-degradation.

However, the current methods and apparatuses for degrading an artificial bone still need to be improved.

SUMMARY

According to an aspect of the present disclosure, the present disclosure proposes an apparatus for invitro control of a degradation rate of an artificial bone. The apparatus comprises: a variable resistor; and a wearable component, comprising: a metal wire electrically connected in series with the variable resistor and configured to generate an alternating magnetic field; and an insulating textile layer covering the metal wire and matching with a shape of an object in which the artificial bone is to be used.

According to an embodiment of the present disclosure, the apparatus further comprises: a controller electrically connected to the variable resistor, and configured to adjust the resistance value of the variable resistor.

According to an embodiment of the present disclosure, the metal wire is arranged as a helix.

According to an embodiment of the present disclosure, the resistance value of the variable resistor is in a range of 0-200 ohms.

According to an embodiment of the present disclosure, the metal wire is formed of a material comprising at least one of copper, aluminum, or gold.

According to an embodiment of the present disclosure, the apparatus further comprises an alternating current power source electrically connected in series with the variable resistor and the metal wire.

According to an embodiment of the present disclosure, the apparatus further comprises a switching element disposed in a series circuit formed of the metal wire, the variable resistor, and the alternating current power source and configured to control on and off of the apparatus.

According to an embodiment of the present disclosure, the wearable component has an accommodating space provided therein, wherein the accommodating space is defined by the metal wire and the insulating textile layer.

According to another aspect of the present disclosure, the present disclosure proposes a method for degrading an artificial bone in situ using the apparatus described above. According to an embodiment of the present disclosure, the method comprises: adjusting the resistance value of the variable resistor to control strength of the alternating magnetic field of the apparatus, so as to control the degradation rate of the artificial bone.

According to an embodiment of the present disclosure, the step of adjusting the resistance value of the variable resistor to control strength of the alternating magnetic field of the apparatus comprises steps of: determining the strength of the alternating magnetic field of the apparatus according to a predetermined degradation rate of the artificial bone; and determining the resistance value of the variable resistor according to the strength of the alternating magnetic field of the apparatus.

According to an embodiment of the present disclosure, the degradation rate of the artificial bone is proportional to the strength of the alternating magnetic field of the apparatus.

According to an embodiment of the present disclosure, the strength of the alternating magnetic field of the apparatus is inversely proportional to the resistance value of the variable resistor.

According to an embodiment of the present disclosure, the artificial bone is a magnesium alloy bone having a protective film provided on a surface thereof, and the method further comprising: adjusting the resistance value of the variable resistor according to the degradation rate of the protective film.

According to an embodiment of the present disclosure, after the protective film is degraded, the method further comprises: increasing the resistance value of the variable resistor according to a predetermined degradation rate of the magnesium alloy bone.

According to yet another aspect of the present disclosure, the present disclosure proposes an artificial bone which is degradable by using the apparatus described above. According to an embodiment of the present disclosure, the artificial bone comprises: a titanium alloy bone; and/or a magnesium alloy bone having a protective film provided on a surface thereof.

According to an embodiment of the present disclosure, the protective film is formed by a passivation process.

According to an embodiment of the present disclosure, the passivation process comprises a heat process in an oxygen-free environment and an oxidation process in a pure oxygen environment.

According to an embodiment of the present disclosure, the heat process is performed at a temperature of 200 to 300 degrees Celsius, and the oxidation process is performed for 2-3 hours.

BRIEF DESCRIPTION OF THE DRAWINGS

The above and/or additional aspects and advantages of the present disclosure will become apparent and readily understood from the description of the embodiments in conjunction with the following accompanying drawings, in which.

DETAILED DESCRIPTION

The embodiments of the present disclosure will be described in detail below, and examples of the embodiments are illustrated in the accompanying drawings, in which the same or similar reference signs are used to refer to the same or similar elements or elements having the same or similar functions. The embodiments described below with reference to the accompanying drawings are intended to be illustrative, and are only used to explain the present disclosure, but may not be construed as limiting the present disclosure.

Currently, artificial bones have poor effect on improvement of self-repair of human bones. The inventors have conducted in-depth researches and a large number of experiments and found that this is mainly due to the fact that a degradation rate of the artificial bones may not be controlled currently during the repair of broken bones. Specifically, the current degradation of the artificial bones is usually self-degradation, that is, self-degradation of the artificial bones occurs through exchange of electrons with fluids in a human body. The above process is a self-reaction process, and it is impossible to control the degradation rate of the artificial bones. When there is a difference between the degradation rate of the artificial bones and a recovery rate of the human body, it may affect the assistance effect on the repair of the human bones, or may even cause other injuries which increase patients' pain.

Some embodiments of the present disclosure are directed to at least alleviate or solve at least one of the problems described above to some extent.

Figure 1:
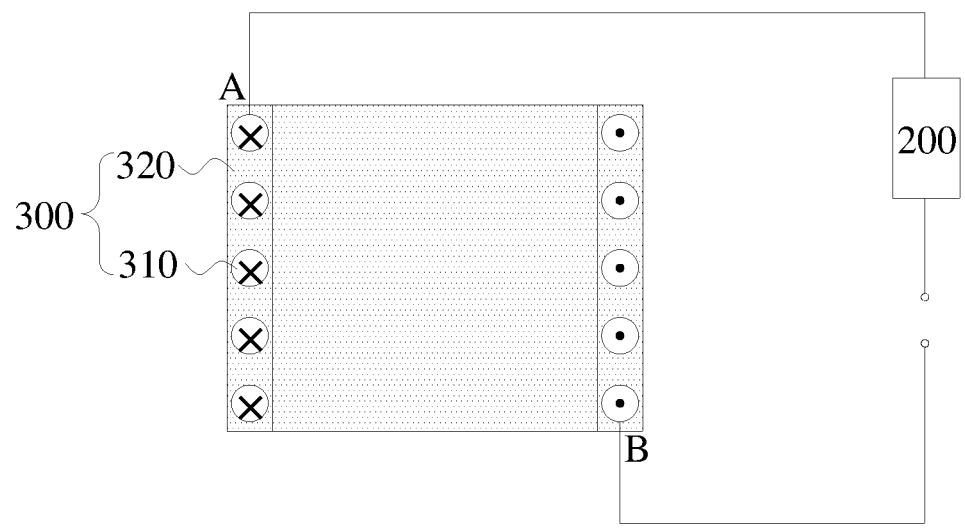
FIG. 1 illustrates a schematic structural diagram of an apparatus for invitro control of a degradation rate of an artificial bone according to an embodiment of the present disclosure.

In one aspect of the present disclosure, the present disclosure proposes an apparatus for invitro control of a degradation rate of an artificial bone. According to the embodiment of the present disclosure, as shown in FIG. 1, the apparatus comprises a variable resistor 200 and a wearable component 300. Here, the wearable component 300 comprises metal wire 310 for generating an alternating magnetic field and an insulating textile layer 320. The insulating textile layer 320 covers the metal wire 310 and matches with a shape of an object in which the artificial bone is to be used (e.g. a part of a human body, such as an ankle, a knee, etc.), and the metal wire 310 are connected in series with the variable resistor 200. Thus, the degradation rate of the artificial bone may be controlled using the apparatus, so that the degradation rate of the artificial bone matches a recovery rate of a human body.

For convenience of understanding, the apparatus according to the embodiment of the present disclosure will be firstly described in brief below.

As described above, the current degradation of the artificial bones is usually self-degradation, that is, self-degradation of the artificial bones occurs through exchange of electrons with fluids in a human body. The above process is a self-reaction process, and it is impossible to control a degradation rate of the artificial bones during repair of broken bones. When there is a difference between the degradation rate of the artificial bones and a recovery rate of the human body, it may affect the assistance effect on the repair of the human bones, or may even cause other injuries which increase patients' pain.

According to the embodiment of the present disclosure, the apparatus may adjust intensity of an alternating magnetic field in the apparatus by adjusting a resistance value of the variable resistor, wherein the strength of the alternating magnetic field may affect a rate at which electrons are exchanged between the artificial bone and the fluids in the human body, so as to control the degradation rate of the artificial bone. In this way, the degradation rate of the artificial bone matches the recovery rate of the human body, so that the human bone may be healed better, and thereby the artificial bone has a good assistance effect on the repair of the human bone.

Various structures of the apparatus will be described in detail below according to specific embodiments of the present disclosure.

Figure 2:
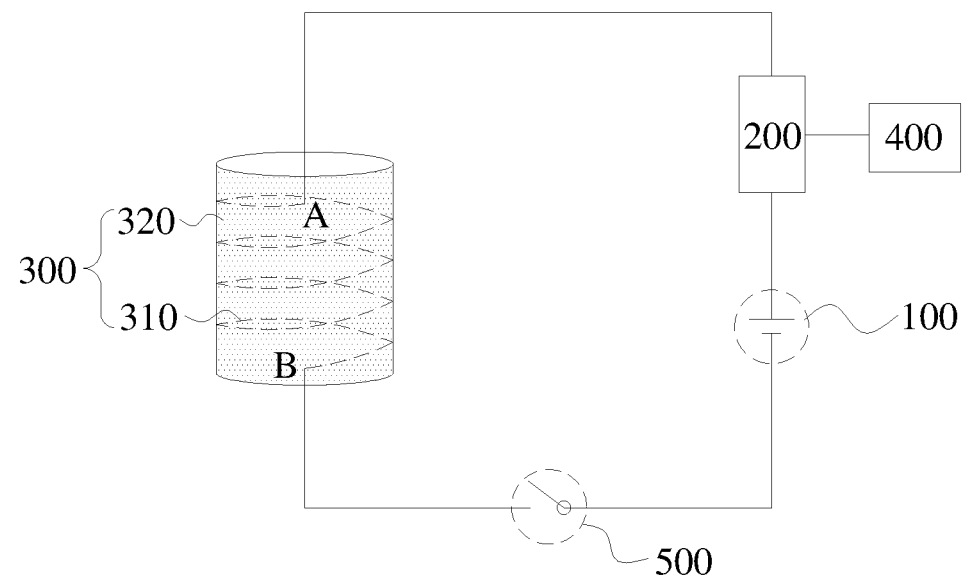
FIG. 2 illustrates a schematic structural diagram of an apparatus for invitro control of a degradation rate of an artificial bone according to another embodiment of the present disclosure.

According to an embodiment of the present disclosure, as shown in FIG. 2, the apparatus may further comprise an Alternating Current (AC) power source 100 connected in series with the variable resistor 200 and the metal wire 310. Thereby, the apparatus may be provided with alternating current through the AC power source to generate an alternating magnetic field.

According to an embodiment of the present disclosure, as shown in FIG. 2, the metal wire 310 is arranged as a helix. Thereby, the wearable component is formed to have a solenoid structure, and may generate an alternating magnetic field when alternating current is applied to the wearable component, which enables the apparatus to realize a function of controlling the degradation rate of the artificial bone. According to a specific embodiment of the present disclosure, the wearable component 300 may comprise an accommodating space defined by the metal wire 310 and the insulating textile layer 320, that is, the wearable component 300 may be in a cylindrical shape. When the degradation of the artificial bone is controlled in vitro using the apparatus, the accommodating space is a detection area, and a patient only needs to wear the wearable component 300 on a part to be repaired. That is, the insulating textile layer 320 may be in a cylindrical shape, and the metal wire 310 is arranged as a helix from top to bottom along inner sidewalls of the insulating textile layer 320 in the insulating textile layer 320 in a cylindrical shape (as shown in FIG. 2). Thereby, when alternating current is applied to the metal wire, an alternating magnetic field may be generated.

However, it should be illustrated that the embodiments of the present disclosure are not limited to shapes and/or arrangements described above. For example, the insulating textile layer 320 may have other shapes, for example, a regular shape such as a prism, a truncated cone, or a frustum of a prism etc., or may have an irregular shape, such as a glove shape which fits a curve of a hand, a kneepad shape which fits a curve of a knee etc. Further, a spatial structure of the metal wire 310 is not limited to the solenoid, but may be a structure which varies depending on a shape of the insulating textile layer 320 as long as it may generate an alternating magnetic field.

According to the embodiment shown in FIG. 1, the metal wire 310 are connected in series with the variable resistor 200 and the alternating current power source 100. Specifically, the metal wire 310 is arranged as a helix, and the metal wire 310 have two connection terminals, of which one (for example, terminal A shown in FIG. 2) is connected to the variable resistor 200 through a wire, and the other (for example, terminal B shown in FIG. 2) is connected to the AC power source 100 through a wire. Thereby, the strength of the alternating magnetic field of the wearable component may be adjusted by adjusting the resistance value of the variable resistor.

According to a specific embodiment of the present disclosure, as shown in FIGS. 1 and 2, the variable resistor 200 may be connected to a positive electrode of the alternating current power source 100. In this case, current is output from the positive electrode of the alternating current power source 100, passes through the variable resistor 200, is then input into the metal wire 310 through the terminal A (shown as x in FIG. 1, which indicates that a direction of the current is inwardly perpendicular to a paper plane), is output from the metal wire 310 through the B terminal (shown as • in FIG. 1, which indicates that the direction of the current is outwardly perpendicular to the paper plane), and returns to a negative electrode of the AC power source 100 through a wire. Thus, when the current passes through the metal wire, the metal wire may generate an alternating magnetic field, and since the metal wire are connected in series with the variable resistor, strength of the alternating magnetic field generated by the metal wire may be adjusted by adjusting the resistance value of the variable resistor.

A material of which the metal wire are formed is not particularly limited as long as it has good electrical conductivity, and may be designed by those skilled in the art according to specific conditions. For example, according to an embodiment of the present disclosure, the metal wire 310 may be formed of a material comprising at least one of copper, aluminum, or gold. Thereby, if a metal wire is formed of the above material, the metal wire may have good electrical conductivity. According to an embodiment of the present disclosure, the insulating textile layer 320 may be formed of an elastic insulating textile material, and thereby the wearable component may be expanded and contracted to be suitable for use by different patients. A size of the metal wire is not particularly limited as long as a helix arrangement of the metal wire in the insulating textile layer may be realized to achieve its usage function, and may be designed by those skilled in the art according to specific conditions. For example, the metal wire are designed according to a size of a specific part under test (such as a leg, an arm, etc.), so that the apparatus may be suitable for degradation of artificial bones at different parts.

According to an embodiment of the present disclosure, the variable resistor 200 may have a resistance value in a range from 0Ω to 200Ω, but the present disclosure is not limited thereto. Thereby, strength of an alternating magnetic field suitable for degradation of the artificial bone may be obtained by adjusting the resistance value of the variable resistor within the resistance value range described above. According to an embodiment of the present disclosure, when the resistance value of the variable resistor 200 is adjusted to a small resistance value, large current passes through the metal wire 310, so that the alternating magnetic field generated by the metal wire 310 which is arranged as a helix has large strength, which may accelerate exchange of electrons between the artificial bone and the fluids in the human body, so as to accelerate the degradation of the artificial bone. In a process of using the apparatus, the degradation rate of the artificial bone may be determined according to the recovery rate of the human body, the strength of the alternating magnetic field required to be generated by the apparatus is determined according to the degradation rate of the artificial bone, and a specific resistance value to which the variable resistor is required to be adjusted is determined according to the strength of the alternating magnetic field of the apparatus. Thus, the degradation rate of the artificial bone may be controlled invitro using the apparatus, so that the degradation rate of the artificial bone matches the recovery rate of the human body.

According to an embodiment of the present disclosure, as shown in FIG. 2, the apparatus may further comprise: a controller 400 connected to the variable resistor 200, and configured to adjust the resistance value of the variable resistor 200. Therefore, the controller 400 may be used to adjust the resistance value of the variable resistor 200, so as to realize the adjustment of the strength of the alternating magnetic field of the apparatus, thereby realizing the adjustment of the degradation rate of the artificial bone, so that the degradation rate of the artificial bone matches the recovery rate of the human body.

According to an embodiment of the present disclosure, as shown in FIG. 2, the apparatus may further comprise a switching element 500 disposed in a series circuit formed of the metal wire 310, the variable resistor 200, and the alternating current power source 100 and configured to control on and off of the apparatus, which is convenient for use.

In another aspect of the present disclosure, the present disclosure proposes a method for degrading an artificial bone in situ using the apparatus described above. According to an embodiment of the present disclosure, the method comprises: adjusting the resistance value of the variable resistor in the apparatus to control the strength of the alternating magnetic field of the apparatus, so as to control the degradation rate of the artificial bone. Thus, the adjustment of the degradation rate of the artificial bone may be achieved using a simple method, which is a very simple and convenient adjustment manner.

According to an embodiment of the present disclosure, adjusting the resistance value of the variable resistor in the apparatus to control the strength of the alternating magnetic field of the apparatus may comprise: firstly, determining the intensity of the alternating magnetic field required to be generated by the apparatus according to a predetermined degradation rate of the artificial bone, and then determining the resistance value of the variable resistor in the apparatus according to the strength of the alternating magnetic field required to be generated by the apparatus. It should be illustrated that the predetermined degradation rate of the artificial bone may be determined according to the recovery rate of the human body. After determining the degradation rate of the artificial bone according to the recovery rate of the human body, the intensity of the alternating magnetic field which controls the degradation rate of the artificial bone may be determined, so that the resistance value of the variable resistor required for acquiring the strength of the alternating magnetic field may be determined. Thereby, after the variable resistor is adjusted according to the resistance value of the variable resistor, the degradation rate of the artificial bone may match the recovery rate of the human body, so that the human bone may be healed better, and thereby the artificial bone has a good assistance effect on the repair of the human bone.

According to an embodiment of the present disclosure, the degradation rate of the artificial bone is proportional to the strength of the alternating magnetic field of the apparatus, and the strength of the alternating magnetic field of the apparatus is inversely proportional to the resistance value of the variable resistor. Therefore, the adjustment of the degradation rate of the artificial bone may be realized by adjusting the resistance value of the variable resistor, which is a very simple and convenient adjustment manner. Specifically, when the variable resistor in the apparatus has a small resistance value, large current is input into the metal wire, and thereby the metal wire generate an alternating magnetic field with large strength. That is, the strength of the alternating magnetic field of the apparatus is inversely proportional to the resistance value of the variable resistor. The alternating magnetic field with large strength may accelerate a rate at which electrons are exchanged between the artificial bone and the fluids in the human body, thereby accelerating the degradation of the artificial bone. That is, the degradation rate of the artificial bone is proportional to the strength of the alternating magnetic field of the apparatus.

For convenience of understanding, a principle of the method for degrading an artificial bone according to an embodiment of the present disclosure will be described in brief below.

Figure 3:
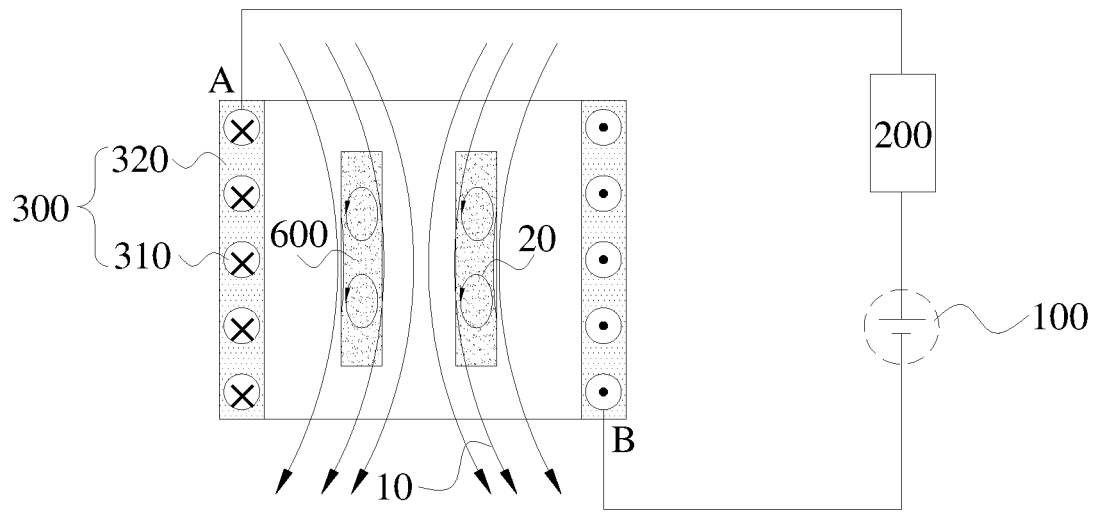
FIG. 3 illustrates a schematic diagram of degrading an artificial bone using an apparatus for invitro control of a degradation rate of an artificial bone according to an embodiment of the present disclosure.

According to an embodiment of the present disclosure, as shown in FIG. 3, after current is output from the alternating current power source 100, the current is input into the wearable component 300 through the variable resistor 200, wherein the current is input into the metal wire 310 through the terminal A and is output from the metal wire 310 through the terminal B. The metal wire 310 may generate an alternating magnetic field 10 due to the current being input therein, and the alternating magnetic field 10 may form induced eddy current 20 on a surface of an artificial bone 600. The induced eddy current 20 may accelerate exchange of electrons between the artificial bone 600 and the fluids in the human body. Thereby, electrochemical corrosion of the artificial bone 600 is aggravated, which realizes control of the degradation rate of the artificial bone through the alternating magnetic field. Further, adjustment of the strength of the alternating magnetic field of the apparatus may be realized by adjusting the resistance value of the variable resistor. Thus, the strength of the alternating magnetic field of the apparatus may be adjusted by adjusting the resistance value of the variable resistor, so as to adjust the degradation rate of the artificial bone.

For convenience of understanding, a process of repairing a broken bone using the apparatus will be described in brief below.

Firstly, an artificial bone is manufactured using a manufacturing method such as casting or forging etc. according to a shape of a human bone of a patient. Subsequently, the manufactured artificial bone is implanted into a part of a human body which needs to be repaired, so as to fix the broken human bone. Then, the patient needs to be reexamined regularly every month to confirm a growth state of the human bone. Finally, after the human bone is grown completely, the wearable component of the apparatus is worn, and the resistance value of the variable resistor of the apparatus is adjusted according to a recovery rate of the human body to adjust a degradation rate of the artificial bone, so that degradation of the artificial bone is completed at the same time when the human body is recovered completely. That is, the degradation rate of the artificial bone matches the recovery rate of the human body.

It should be illustrated that before the broken human bone is grown completely, self-degradation of the artificial bone may occur, that is, electrons are spontaneously exchanged between the artificial bone and the fluids in the human body, and the above self-degradation usually occurs at a low speed, which may ensure a function of fixing the human bone by the artificial bone, thereby ensuring the stability of the growth of the human bone. After the human bone is grown completely, the artificial bone of which self-degradation occurs at a low speed may limit the healing of the human bone. Therefore, the apparatus is worn, which may accelerate the subsequent degradation of the artificial bone, so that the degradation rate of the artificial bone matches the recovery rate of the human body. Thereby, degradation of the artificial bone may also be completed at the same time when the human body is recovered completely.

According to an embodiment of the present disclosure, when self-degradation of the artificial bone, for example, a magnesium alloy bone, occurs at a relatively high speed, a dense protective film, which has a low self-degradation rate, may be provided on a surface of the artificial bone. Therefore, before the human bone is grown completely, self-degradation of the artificial bone is actually self-degradation of the protective film on the surface of the artificial bone. Since the protective film has a low self-degradation rate, a function of fixing the human bone by the artificial bone may be ensured, thereby ensuring the stability of the growth of the human bone. After the human bone is grown completely, the protective film may firstly be destroyed by wearing the apparatus, to expose the internal artificial bone, and the degradation of the exposed artificial bone is accelerated by adjusting the resistance value of the variable resistor, so that the degradation rate of the exposed artificial bone matches the recovery rate of the human body. Thereby, degradation of the artificial bone is completed at the same time when the human body is recovered completely.

According to an embodiment of the present disclosure, when the artificial bone is a magnesium alloy bone having a protective film provided on a surface thereof, the method may comprise: after the human bone is grown completely, firstly adjusting the resistance value of the variable resistor according to the degradation rate of the protective film described above. Thus, the resistance value of the variable resistor is adjusted, so that the strength of the alternating magnetic field of the apparatus may be adapted to degrade the protective film, so as to destroy the protective film on the surface of the magnesium alloy bone, thereby accelerating the degradation of the magnesium alloy bone. According to a specific embodiment of the present disclosure, the resistance value of the variable resistor may be adjusted to a minimum value, in which case, the largest current is input into the metal wire, and the alternating magnetic field generated by the metal wire has the largest intensity. Thereby, the protective film may be degraded at a relatively high speed, to destroy the protective film, thereby exposing the internal magnesium alloy bone.

Subsequently, the resistance value of the variable resistor is increased according to the predetermined degradation rate of the magnesium alloy bone. Therefore, after the protective film is destroyed, the resistance value of the variable resistor is adjusted, so that the strength of the alternating magnetic field of the apparatus may be adapted to degrade the magnesium alloy bone, so as to realize the adjustment of the degradation rate of the magnesium alloy bone, so that the degradation rate of the magnesium alloy bone matches the recovery rate of the human body.

It should be illustrated that the protective film has a relatively high density, so that the self-degradation rate of the protective film is lower than that of the magnesium alloy bone. Therefore, when the protective film is degraded, an alternating magnetic field with large strength is required to destroy the protective film, and when the magnesium alloy bone is degraded, an alternating magnetic field with lower strength is required for the degradation as compared with the protective film. Therefore, after the protective film is destroyed, the resistance value of the variable resistor is increased, so that the strength of the alternating magnetic field for degrading the magnesium alloy bone is suitable for the magnesium alloy bone to complete the degradation of the magnesium alloy bone. In subsequent degradation of the exposed magnesium alloy bone, a degradation rate of the magnesium alloy bone needs to match the recovery rate of the human body, so that the degradation of the magnesium alloy bone may also be completed at the same time when the human body is recovered completely.

In another aspect of the present disclosure, the present disclosure proposes an artificial bone which may be degraded using the apparatus described above. According to an embodiment of the present disclosure, the artificial bone comprises: a titanium alloy bone and/or a magnesium alloy bone having a protective film provided on a surface thereof. Thus, the artificial bone may be degraded using the apparatus described above, so that a degradation rate of the artificial bone matches a recovery rate of a human body.

According to an embodiment of the present disclosure, when the artificial bone is a titanium alloy bone, after the human bone is grown completely, it only needs to directly adjust the resistance value of the variable resistor, to ensure that a degradation rate of the titanium alloy bone matches the recovery rate of the human body. Thereby, degradation of the titanium alloy bone may be completed at the same time when the human body is recovered completely. When the artificial bone is a magnesium alloy bone having a protective film provided on a surface thereof, after the human bone is grown completely, it needs to firstly adjust the resistance value of the variable resistor to destroy the protective film, and then adjust the resistance value of the variable resistor, so that a degradation rate of the magnesium alloy bone matches the recovery rate of the human body. Thereby, degradation of the magnesium alloy bone may be completed at the same time when the human body is recovered completely.

According to an embodiment of the present disclosure, the artificial bone may be a titanium alloy bone, or may also be a magnesium alloy bone having a protective film provided on a surface thereof. After the artificial bone is implanted into the human body, regardless of self-degradation of the artificial bone or degradation of the artificial bone using the apparatus, exchange reaction of electrons between the artificial bone and fluids in the human body occurs. After the exchange of electrons between the artificial bone and the fluids in the human body occurs, titanium ions or magnesium ions produced in the human body may not have toxic effects on the human body even if the titanium ions or the magnesium ions have a high concentration. Therefore, materials of the above artificial bone are safe and effective.

According to an embodiment of the present disclosure, the protective film on the surface of the magnesium alloy bone may be formed by a passivation process. Thus, the protective film has a high density, which ensures the stability of the artificial bone before the patient's bone is grown completely. According to an embodiment of the present disclosure, the passivation process may comprise a heat process in an oxygen-free environment and an oxidation process in a pure oxygen environment. Specifically, the magnesium alloy bone is firstly heated to 200-300 degrees Celsius in the oxygen-free environment, and then the heated magnesium alloy bone is placed in the pure oxygen environment for 2-3 hours to form a dense oxide film on the surface of the magnesium alloy bone to hinder degradation of the internal magnesium alloy bone, so as to ensure the stability of the magnesium alloy bone before the human bone is grown completely.

According to an embodiment of the present disclosure, before the magnesium alloy bone is heated in the oxygen-free environment, an oxide layer on the surface of the magnesium alloy bone may be firstly removed in the oxygen-free environment to ensure the cleanliness of the surface of the magnesium alloy bone and better quality of the oxide film which is to be grown subsequently in the pure oxygen environment, so as to improve the performance of the protective film.

Figure 4:
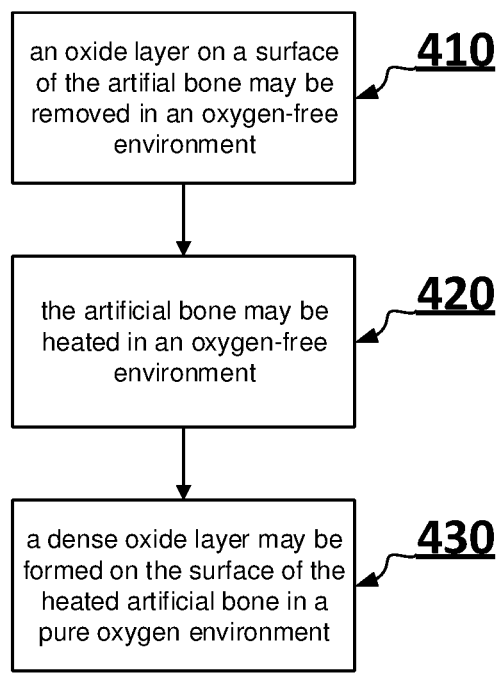
FIG. 4 illustrates a flow chart of a method for processing a magnesium alloy bone according to an embodiment of the present application.

FIG. 4 is a flow chart illustrating a method 400 for processing a artificial bone to form a protective film on its surface according to an embodiment of the present application.

As shown in FIG. 4, the method 400 may begin at the step S410 where an oxide layer on a surface of the artificial bone may be removed in an oxygen-free environment, to prepare an oxide-free surface for subsequent steps. For example, the initial oxide layer may be removed by acid or etching.

At step S420, the artificial bone may be heated in an oxygen-free environment. For example, the artificial bone may be heated at a temperature of 200 to 300 degrees Celsius.

At step S430, a dense oxide layer may be formed on the surface of the heated artificial bone in a pure oxygen environment as a protective film for the artificial bone. For example, the dense oxide layer may be formed after the oxidation process lasted for 2-3 hours.

Based on the method 400, an artificial bone which may be degradable by using the method described above can be produced.

In the description of the present disclosure, an orientation or position relation indicated by terms such as "up", "down" etc. is based on an orientation or position relation shown in the accompanying drawings, and is merely used to conveniently describe the present disclosure, instead of requiring that the present disclosure must be constructed and operated in a particular orientation, and thus cannot be construed as limiting the present disclosure.

In the description of the present specification, the description made with reference to the terms "one embodiment", "another embodiment" etc. means that specific features, structures, materials or characteristics described in connection with the embodiment are included in at least one embodiment of the present disclosure. In the present specification, schematic expression of the above terms is not necessarily directed to the same embodiment or example. Further, the specific features, structures, materials, or characteristics described may be combined in a suitable manner in any one or more embodiments or examples. In addition, various embodiments or examples described in the specification as well as features of various embodiments or examples may be combined and integrated by those skilled in the art without contradiction. In addition, it should be illustrated that in the present specification, the terms "first" and "second" are used for descriptive purposes only, and are not to be construed as indicating or implying a relative importance or implicitly indicating a number of technical features indicated.

Although the embodiments of the present disclosure have been shown and described above, it may be understood that the above embodiments are illustrative and are not to be construed as limiting the present disclosure. Changes, modifications, substitutions and variations may be made by those of ordinary skill in the art to the above embodiments within the scope of the present disclosure.

We claim:

1. A method for degrading an artificial bone in situ using an apparatus for invitro control of a degradation rate of an artificial bone, the apparatus comprising: a variable resistor; and a wearable component, the wearable component comprising: a metal wire electrically connected in series with the variable resistor and configured to generate an alternating magnetic field; and an insulating textile layer covering the metal wire and matching with a shape of an object in which the artificial bone is to be used, the method comprising:
    adjusting a resistance value of the variable resistor to control strength of the alternating magnetic field of the apparatus, so as to control the degradation rate of the artificial bone.

2. The method according to claim 1, wherein the step of adjusting the resistance value of the variable resistor to control strength of the alternating magnetic field of the apparatus comprises steps of:
    determining the strength of the alternating magnetic field of the apparatus according to a predetermined degradation rate of the artificial bone; and
    determining the resistance value of the variable resistor according to the strength of the alternating magnetic field of the apparatus.

3. The method according to claim 2, wherein the degradation rate of the artificial bone is proportional to the strength of the alternating magnetic field of the apparatus.

4. The method according to claim 3, wherein the strength of the alternating magnetic field of the apparatus is inversely proportional to the resistance value of the variable resistor.

5. The method according to claim 1, wherein the artificial bone is a magnesium alloy bone having a protective film provided on a surface thereof, and the method further comprises:
    adjusting the resistance value of the variable resistor according to the degradation rate of the protective film.

6. The method according to claim 5, wherein after the protective film is degraded, the method further comprises:
    increasing the resistance value of the variable resistor according to a predetermined degradation rate of the magnesium alloy bone.

7. An artificial bone which is degradable by using the apparatus method according to claim 1, the artificial bone comprising:
    a titanium alloy bone; and/or
    a magnesium alloy bone having a protective film provided on a surface thereof.

8. A method of processing the artificial bone according to claim 7, the method comprising:
    removing an oxide layer on a surface of the artificial bone in an oxygen-free environment;
    heating the artificial bone in an oxygen-free environment; and
    forming a dense oxide layer on the surface of the artificial bone in a pure oxygen environment.

9. The method according to claim 8, wherein the step of removing an oxide layer on a surface of the artificial bone comprises:
    removing the oxide layer by acid.

10. The method according to claim 8, wherein the step of heating is performed at a temperature of 200 to 300 degrees Celsius.

11. The method according to claim 8, wherein the step of forming the dense oxide layer is performed for 2-3 hours.

12. The method according to claim 1, wherein the apparatus further comprises:
    a controller electrically connected to the variable resistor, and configured to adjust the resistance value of the variable resistor.

13. The method according to claim 1, wherein the metal wire is arranged as a helix.

14. The method according to claim 1, wherein the resistance value of the variable resistor is in a range of 0-200 ohms.

15. The method according to claim 1, wherein the metal wire is formed of a material comprising at least one of copper, aluminum, or gold.

16. The method according to claim 1, wherein the apparatus further comprises an alternating current power source electrically connected in series with the variable resistor and the metal wire.

17. The method according to claim 16, wherein the apparatus further comprises a switching element disposed in a series circuit formed of the metal wire, the variable resistor, and the alternating current power source and configured to control on and off status of the apparatus.

18. The method according to claim 1, wherein the wearable component has an accommodating space provided therein, wherein the accommodating space is defined by the metal wire and the insulating textile layer.

* * * * *